(12) United States Patent
Bergheim

(10) Patent No.: US 8,430,902 B2
(45) Date of Patent: Apr. 30, 2013

(54) METHOD AND ASSEMBLY FOR DISTAL EMBOLIC PROTECTION

(75) Inventor: Bjarne Bergheim, Mission Viejo, CA (US)

(73) Assignee: Medtronic 3F Therapeutics, Inc., Santa Rosa, CA (US)

(*) Notice: Subject to any disclaimer, the term of this patent is extended or adjusted under 35 U.S.C. 154(b) by 592 days.

(21) Appl. No.: 12/580,525

(22) Filed: Oct. 16, 2009

(65) Prior Publication Data
US 2010/0036474 A1 Feb. 11, 2010

Related U.S. Application Data

(60) Division of application No. 10/938,410, filed on Sep. 10, 2004, now Pat. No. 7,604,650, which is a continuation-in-part of application No. 10/680,717, filed on Oct. 6, 2003, now abandoned, and a continuation-in-part of application No. 10/831,770, filed on Apr. 23, 2004.

(51) Int. Cl.
*A61M 29/00* (2006.01)
*A61B 19/00* (2006.01)

(52) U.S. Cl.
USPC .......................................... 606/200; 128/898

(58) Field of Classification Search .................. 606/200, 606/113, 114; 623/1.11–1.21
See application file for complete search history.

(56) References Cited

U.S. PATENT DOCUMENTS

| | | |
|---|---|---|
| 4,419,095 A | 12/1983 | Nebergall et al. |
| 5,370,685 A | 12/1994 | Stevens |
| 5,411,552 A | 5/1995 | Anderson |
| 5,480,424 A | 1/1996 | Cox |
| 5,486,183 A | 1/1996 | Middleman et al. |
| 5,578,076 A | 11/1996 | Krueger et al. |
| 5,713,950 A | 2/1998 | Cox |
| 5,824,063 A | 10/1998 | Cox |
| 5,972,030 A | 10/1999 | Garrison |
| 5,989,281 A | 11/1999 | Barbut et al. |
| 6,092,529 A | 7/2000 | Cox |
| 6,267,783 B1 | 7/2001 | Letendre et al. |
| 6,269,819 B1 | 8/2001 | Oz |
| 6,270,526 B1 | 8/2001 | Cox |
| 6,277,139 B1 | 8/2001 | Levinson et al. |
| 6,425,916 B1 | 7/2002 | Garrison et al. |
| 6,447,539 B1 | 9/2002 | Nelson |
| 6,451,025 B1 | 9/2002 | Jervis |
| 6,458,153 B1 | 10/2002 | Bailey |

(Continued)

FOREIGN PATENT DOCUMENTS

| WO | WO97/17100 | 5/1997 |
|---|---|---|
| WO | WO02/11627 | 2/2002 |

*Primary Examiner* — Tuan V Nguyen

(57) ABSTRACT

Methods and assemblies are described for capturing embolic material in a blood vessel or other body cavity during cardiovascular or valve replacement and repair surgery, wherein access is provided through the apical area of the patient's heart. The distal embolic protection assembly generally comprises a sleeve having a lumen, an actuating member having proximal and distal ends, wherein the actuating member is movably disposed within the lumen, and a filter assembly coupled to the distal end of the actuating member. The filter assembly generally comprises a porous bag having an open proximal end, a collapsible and expandable frame that is coupled to the open proximal end of the porous bag, and at least one support spine disposed at least a part of the longitudinal axis of the porous bag. The porous bag is configured such that it permits blood to perfuse freely through while capturing embolic material and other debris.

22 Claims, 8 Drawing Sheets

U.S. PATENT DOCUMENTS

| | | |
|---|---|---|
| 6,461,366 B1 | 10/2002 | Sequin |
| 6,461,382 B1 | 10/2002 | Cao |
| 6,478,806 B2 | 11/2002 | McFarlane |
| 6,562,020 B1 | 5/2003 | Constantz |
| 6,582,462 B1 | 6/2003 | Anderson |
| 6,589,266 B2 | 7/2003 | Whitcher et al. |
| 6,613,063 B1 | 9/2003 | Hunsberger |
| 6,673,109 B2 | 1/2004 | Cox |
| 6,682,559 B2 | 1/2004 | Myers |
| 6,719,787 B2 | 4/2004 | Cox |
| 6,719,788 B2 | 4/2004 | Cox |
| 6,719,789 B2 | 4/2004 | Cox |
| 6,830,585 B1 | 12/2004 | Artof et al. |
| 6,939,359 B2 | 9/2005 | Tu |
| 2002/0049468 A1 | 4/2002 | Streeter |
| 2002/0161390 A1 | 10/2002 | Mouw |
| 2002/0161394 A1 | 10/2002 | Macoviak et al. |
| 2004/0220608 A1 | 11/2004 | D'Aquanni et al. |
| 2005/0075712 A1 | 4/2005 | Biancucci |
| 2005/0075724 A1 | 4/2005 | Svanidze |
| 2005/0177187 A1 | 8/2005 | Gray et al. |
| 2006/0129180 A1 | 6/2006 | Tsugita et al. |

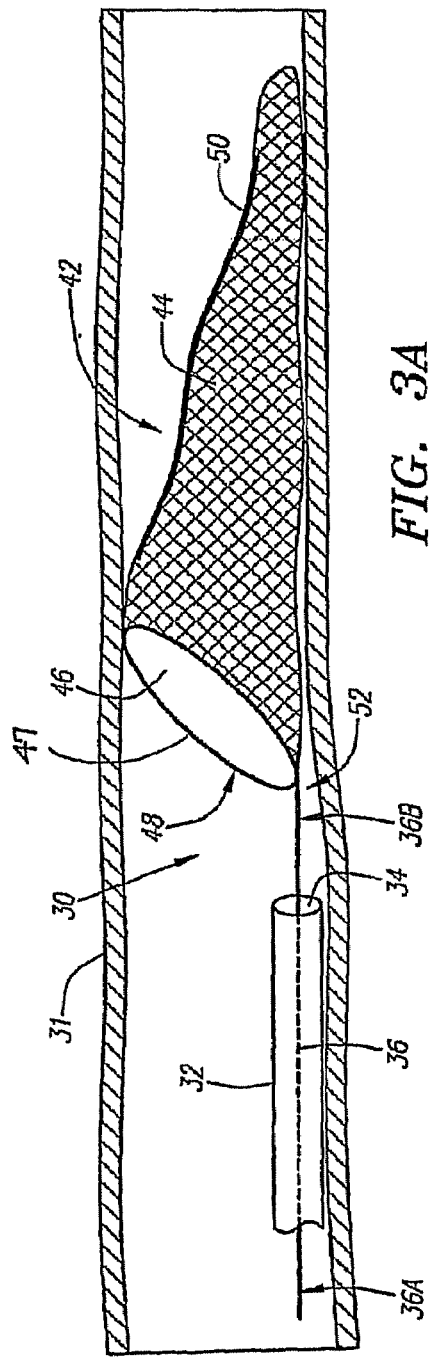
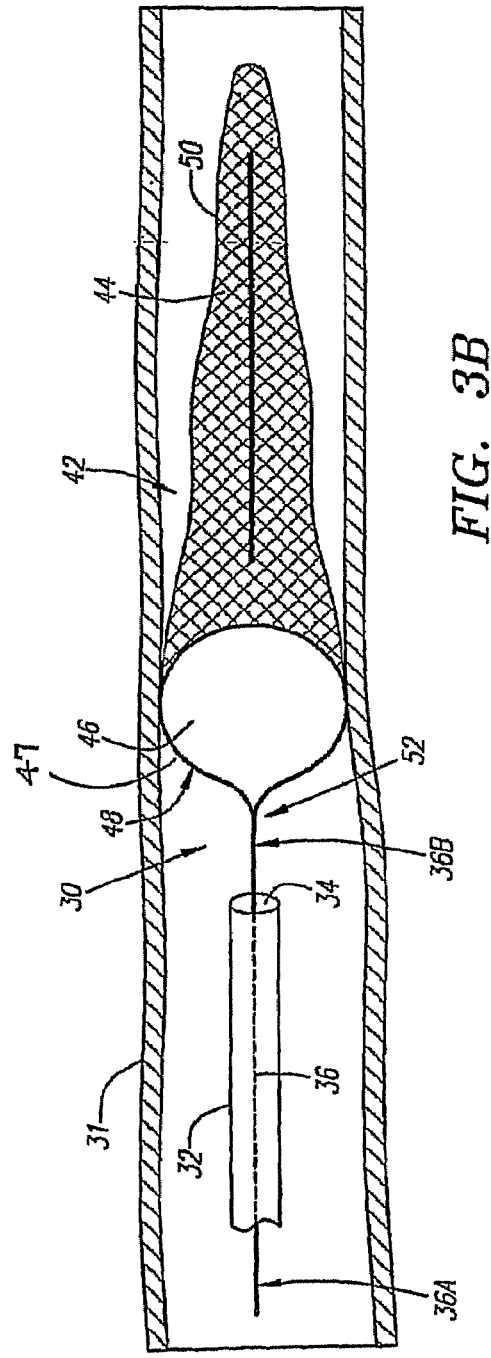

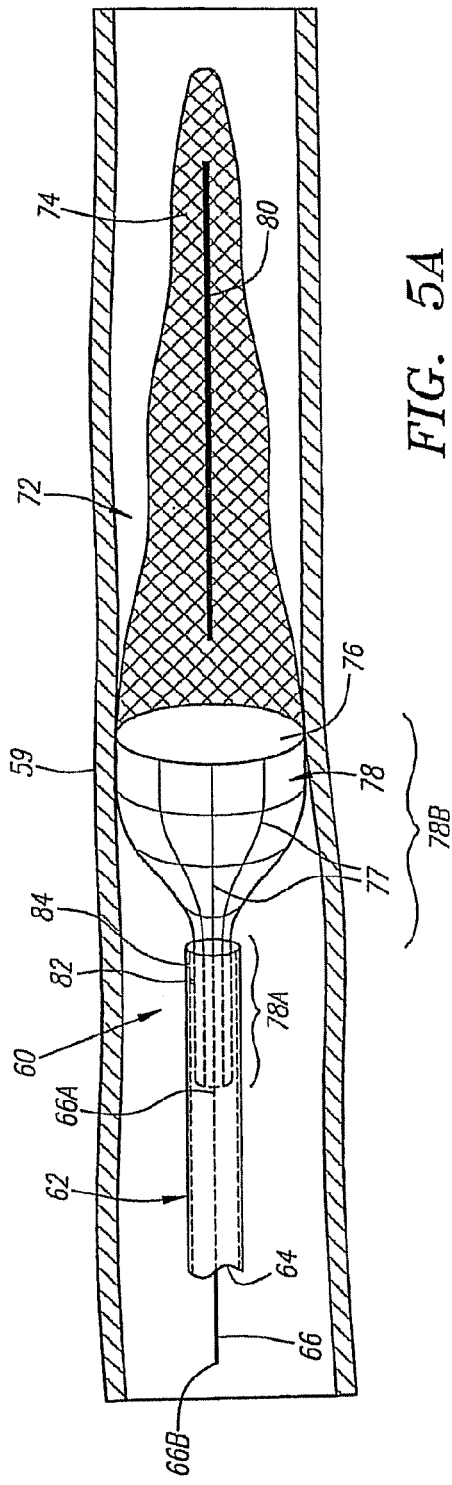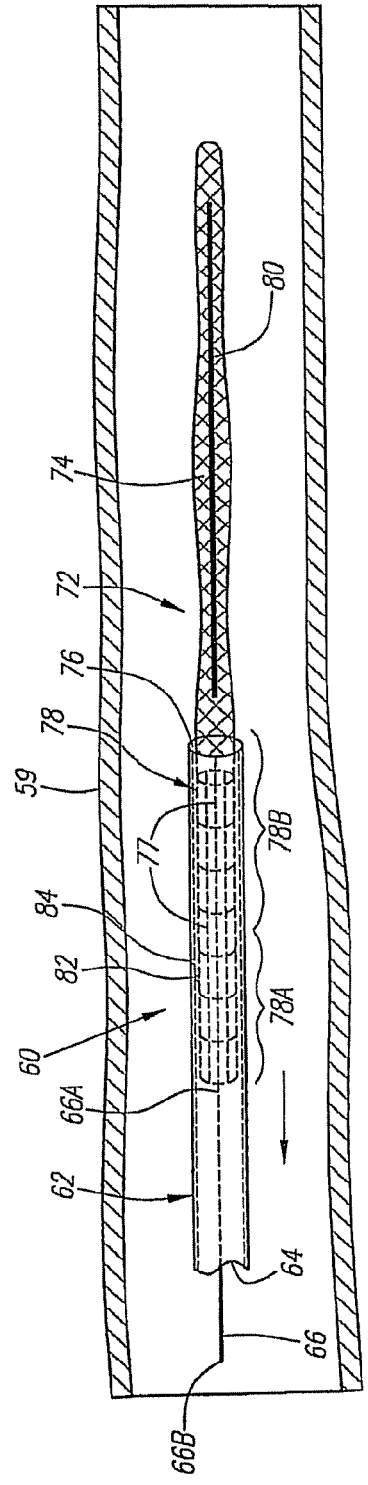

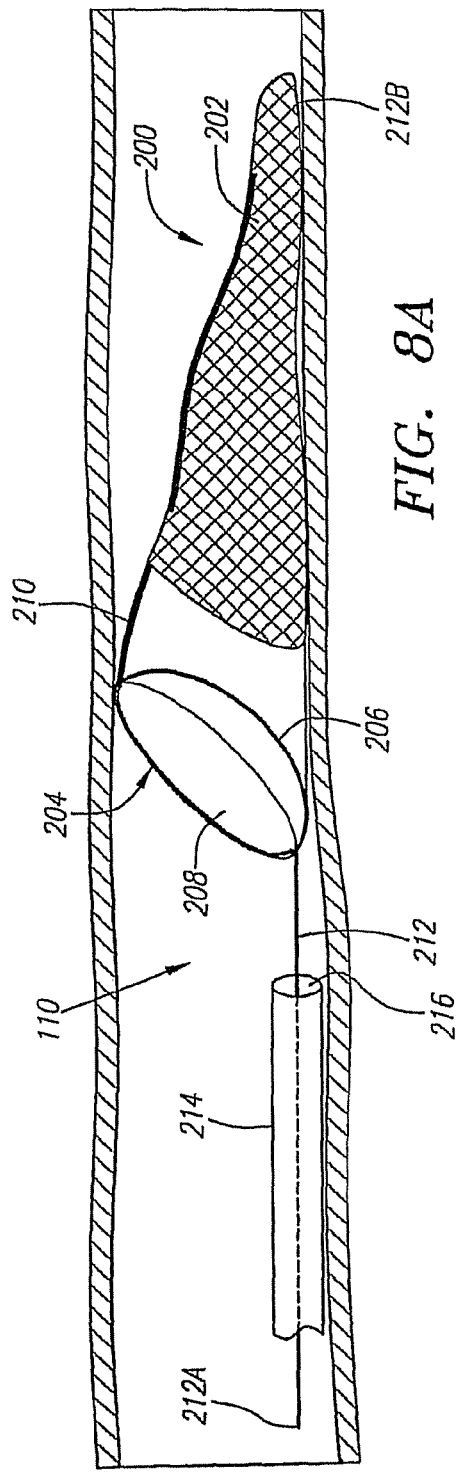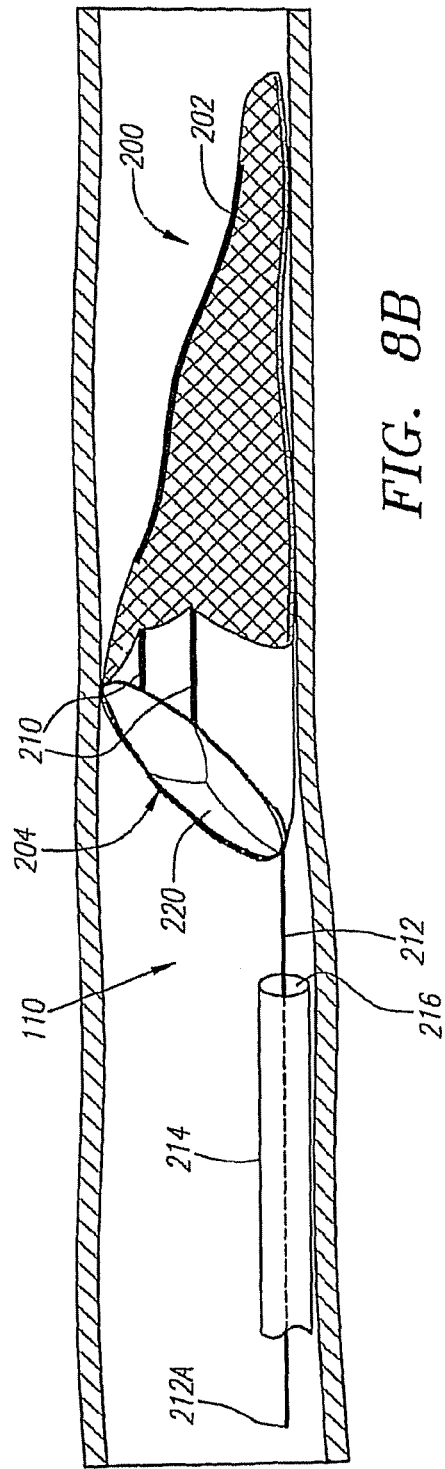

METHOD AND ASSEMBLY FOR DISTAL EMBOLIC PROTECTION

CROSS-REFERENCE TO RELATED APPLICATION

This application is a divisional of and claims priority to patent application Ser. No. 10/938,410, filed Sep. 10, 2004, now U.S. Pat. No. 7,604,650; which is (1) a continuation-in-part of and claims priority to patent application Ser. No. 10/680,717, filed Oct. 6, 2003, now abandoned, and (2) a continuation-in-part of and claims priority to patent application Ser. No. 10/831,770, filed Apr. 23, 2004, now pending, the entirety of which is incorporated by reference in their entirety.

FIELD OF THE INVENTION

The present invention relates generally to methods and systems for cardiovascular surgery. More particularly, the invention relates to methods and systems for capturing embolic or other materials during cardiovascular surgery.

BACKGROUND OF THE INVENTION

Various surgical techniques may be used to repair a diseased or damaged heart valve, such as annuloplasty (contracting the valve annulus), quadrangular resection (narrowing the valve leaflets), commissurotomy (cutting the valve commissures to separate the valve leaflets), or decalcification of valve and annulus tissue. Alternatively, the diseased heart valve may be replaced by a prosthetic valve. Where replacement of a heart valve is indicated, the dysfunctional valve is typically removed and replaced with either a mechanical or tissue valve. Tissue valves are generally preferred over mechanical valves because they typically do not require long-term treatment with anticoagulants.

A number of different strategies have been used to repair or replace a defective heart valve. Open-heart valve repair or replacement surgery is a long and tedious procedure and involves a gross thoracotomy, usually in the form of a median sternotomy. In this procedure, a saw or other cutting instrument is used to cut the sternum longitudinally and the opposing halves of the anterior or ventral portion of the rib cage are spread apart. A large opening into the thoracic cavity is thus created, through which the surgeon may directly visualize and operate upon the heart and other thoracic contents. The patient must be placed on cardiopulmonary bypass for the duration of the surgery.

Open-chest valve replacement surgery has the benefit of permitting the direct implantation of the replacement valve at its intended site. This method, however, is highly invasive and often results in significant trauma, risk of complications, as well as extended hospitalization and painful recovery period for the patient.

Minimally invasive percutaneous valve replacement procedures have emerged as an alternative to open-chest surgery. Unlike open-heart procedures, this procedure is indirect and involves intravascular catheterization from a femoral vessel to the heart. Because the minimally invasive approach requires only a small incision, it allows for a faster recovery for the patient with less pain and the promise of less bodily trauma. This, in turn, reduces the medical costs and the overall disruption to the life of the patient.

The use of a minimally invasive approach, however, introduces new complexities to surgery. An inherent difficulty in the minimally invasive percutaneous approach is the limited space that is available within the vasculature. Unlike open heart surgery, minimally invasive heart surgery offers a surgical field that is only as large as the diameter of a blood vessel. Consequently, the introduction of tools and prosthetic devices becomes a great deal more complicated. The device must be dimensioned and configured to permit it to be introduced into the vasculature, maneuvered therethrough, and positioned at a desired location. This may involve passage through significant convolutions at some distance from the initial point of introduction.

Accordingly, while heart valve surgery produces beneficial results for many patients, numerous others who might benefit from such surgery are either unable or unwilling to undergo the trauma and risks of current techniques. Therefore, what is needed are methods and devices for performing heart valve repair or replacement, as well as other procedures within the heart and great vessels of the heart, that provide greater access to the heart valves than the currently minimally invasive techniques, while at the same time reducing the trauma, risks, recovery time and pain that accompany the more invasive techniques.

To this end, methods and systems for performing cardiovascular surgery by accessing the heart or great vessels through the apical area of the heart are disclosed in co-pending patent application Ser. No. 10/831,770, filed Apr. 23, 2004, which is incorporated herein by reference. The unique anatomical structure of the apical area permits the introduction of various surgical devices and tools. into the heart without significant disruption of the natural mechanical and electrical heart function.

While access to the heart through the femoral vessels in the conventional percutaneous methods are limited to the diameter of the smallest vessel through which it must pass through (typically about 8 mm), access to the heart through the apical area permits a significantly larger and more direct working space (up to approximately 25 mm). By directly access into the heart and great vessels through the apex, there is greater flexibility as to the type, size and capacity of surgical devices to perform valve replacement or repair surgery.

In any valve repair or replacement surgery, however, manipulation of the heavily calcified valves may result in dislodgment of calcium and valve or other surrounding tissue and debris, with subsequent embolization and blockage. Accordingly, there is a risk that embolic material will be dislodged by the procedure and will migrate through the circulatory system and cause clots and strokes. A need therefore exists for safely containing embolic material during cardiovascular surgery.

Various systems and techniques have been proposed for removing debris from the circulatory system in order to prevent the debris from causing any harm. One technique involves temporarily obstructing the artery and then suctioning embolic material, debris and blood from the treatment site. This technique, however, requires that blood flow through the artery be obstructed, causing complete cessation or at least a substantial reduction in blood flow volume during a period of time which can be significant for organ survival. Another technique involves cutting the embolic material into small pieces such that they will not occlude vessels within the vasculature. With this technique, however, it is often difficult to control the size of the fragments which are severed and larger fragments may be severed accidentally.

Thus, there is a need for an apparatus and method for capturing debris that is dislodged during valve repair or replacement surgery which substantially reduces the risk of embolic material escaping to the vessel and causing a blockage at a downstream location. There is also a need for an apparatus and method that can be introduced through the apical area of the patient's heart and positioned in a location downstream from and distal to the area in which the valve repair or replacement surgery is to be performed.

SUMMARY OF THE INVENTION

Methods and systems are provided for capturing embolic material in a blood vessel or other body cavity during cardiovascular or valve replacement and repair surgery, wherein access is provided through the apical area of the patient's heart. In addition to capturing embolic material during cardiovascular procedures, the distal embolic protection assembly may also be used in connection with the removal of native valves, such as valve leaflets, and other valve components and materials which may become dislodged during surgical procedure.

In one embodiment, the distal embolic protection assembly generally comprises a sleeve having a lumen, an actuating member having proximal and distal ends, wherein the actuating member is movably disposed within the lumen of the sleeve, and a filter assembly coupled to the distal end of the actuating member. The filter assembly generally comprises a porous bag having an open proximal end, a collapsible and expandable frame that is coupled to the open proximal end of the porous bag, and at least one support spine disposed at least a part of the longitudinal axis of the porous bag. The porous bag is configured such that it permits blood to perfuse freely through while capturing embolic material and other debris which enters through the open proximal end of the porous bag.

In another embodiment, the frame of the filter assembly is collapsible within the lumen of the sleeve and expandable to a deployed state when unconstrained by the sleeve to substantially conform to a vessel or other body lumen of the patient. The filter assembly may be delivered to the site of implantation within the patient's body in a collapsed state within the lumen of the sleeve. Once filter assembly is positioned at the site, the actuation member may be pushed distally to release the frame from the lumen of the sleeve and deploy the filter assembly within the vessel or other body lumen. After valve or other surgery has completed, the actuation member may be pulled proximally to compress the frame of the filter assembly in a collapsed state within the lumen of the filter. When the frame of the filter assembly is contained with the lumen in this manner, embolic material or other debris contained within the porous bag is not likely to escape out of the porous bag.

In yet another embodiment, the frame of the filter assembly is selected such that it substantially engages open proximal end of the porous bag to the walls of the blood vessel or other body lumen. In one embodiment, the frame of the filter assembly comprises a substantially circular shape or a coil that may be formed from a single piece of shape memory material, such as Nitinol. The substantially circular or coil frames may be actuated between the collapsed and expanded state by manipulation of the actuation member, the sleeve, or relative motion of the actuation member and the sleeve toward one another.

In a further embodiment, the frame of the filter assembly may be a stent frame having longitudinal arms that actuate the stent frame between the collapsed and expanded states. The stent frame may be actuated between the collapsed and expanded state by manipulation of the actuation member, the sleeve, or the relative motion of the actuation member and the sleeve toward one another.

In yet a further embodiment, the frame of the filter assembly may be an inflatable balloon frame that is coupled to the open proximal end of the porous bag. The inflatable balloon frame is substantially donut shaped such that blood and embolic material is permitted to perfuse through the center of the inflatable balloon frame and into the porous bag. The inflatable balloon frame is in fluid communication with a peripheral gas or fluid reservoir through a conduit. Because the balloon may be deflated to a collapsed state, the filter assembly may be introduced into and removed from the vessel or other body lumen with or without the sleeve.

In an alternative embodiment, the frame of the filter assembly may comprise a plurality of arms which converge at the distal end of the actuating member and extend radially outward and are coupled to the open proximal end of the filter assembly. The plurality of arms function to actuate between the collapsed state of the filter assembly when contacts the sleeve and is urged into the lumen of the sleeve. The plurality of arms is biased to an expanded and deployed state when the frame is released from the lumen of the sleeve.

The filter assemblies disclosed herein may further comprise a cloth covering the perimeter of the open proximal end of the porous bag. Used in this manner, the cloth covering will substantially form a seal between the open proximal end and the walls of the blood vessel. Such a seal will ensure that embolic material and debris will not be trapped in or be allowed to pass between the open proximal end of the porous bag and the walls of the blood vessel. In addition, the cloth covering will protect the aortic wall from becoming damaged by the expanding frame of the filter assembly.

Additionally and alternatively, the filter assemblies disclosed herein may further include a one-way valve at the open proximal end of the filter assembly to serve the dual function of acting as a temporary valve during valve replacement surgery and preventing embolic material and debris from escaping out from the filter. The valve permits the natural forward flow of blood and any embolic material into the porous bag and reduces the retrograde flow of blood and embolic material back out of the porous bag. In other words, blood and embolic material are allowed to flow downstream, but not upstream. The addition of a one-way valve also permits surgical interventions on the aortic valve on a beating heart and takes the function of the aortic valve if it is removed or becomes dysfunctional.

The various embodiments of the filter assembly described herein provide various advantages as a result of being deliverable through the apex of the heart. The relative simplicity in the structure and mechanism of the distal protection assembly and, more particularly, the filter assembly, can be seen. For example, the conventional need for fixedly coupling both ends of the filter assembly to a catheter or guidewire for delivery and placement within the blood vessel is now obviated by the distal protection assemblies disclosed herein.

The above aspects and other objects, features and advantages of the present invention will become apparent to those skilled in the art from the following description of the preferred embodiments taken together with the accompanying figures.

BRIEF DESCRIPTION OF THE DRAWINGS

FIG. 3 depicts an embodiment of a distal embolic protection assembly having a substantially circular frame in its deployed and expanded state. FIGS. 3A and 3B are two side views of the distal embolic protection assembly.

FIG. 4 shows the retraction of the filter assembly of FIG. 3 into the lumen of the sleeve to facilitate removal of the distal embolic protection assembly from the patient.

FIG. 5 depicts an embodiment of the distal protection assembly having a stent expandable frame. FIG. 5A shows the filter assembly in its deployed state and FIG. 5B shows the filter assembly in its collapsed state for insertion into or removal from the patient's body.

FIG. 6 illustrates an embodiment in which the frame of the filter assembly comprising a plurality of arms.

FIG. 7 depicts an embodiment of the distal protection assembly having an inflatable balloon frame.

FIG. 8 depicts an embodiment of the distal protection assembly of FIG. 3 having a one-way valve at the open proximal end of the filter assembly. FIG. 8A depicts the filter assembly with a bileaflet valve and FIG. 8B depicts the filter assembly with a trileaflet valve.

DESCRIPTION OF THE PREFERRED EMBODIMENTS

The advantages of performing valve repair or replacement surgery through the apical area of a patient's heart have been described in co-pending patent application Ser. No. 10/831,770, filed Apr. 23, 2004, which is incorporated herein by reference. The apical approach is significantly less invasive than open-chest techniques and it provides a more direct surgical approach to the valves and great vessels of the heart than the conventional minimally invasive percutaneous techniques. Moreover, because the apical approach can accommodate a larger incision and does not require maneuvering through long convolutions of the vasculature from the femoral arteries, it is not limited by the size constraints of the percutaneous techniques. Moreover, percutaneous methods may not be suitable in patients with severe atherosclerosis in which the vasculature is substantially narrowed.

The apical approach to valve replacement surgery is particularly suited for replacement of heart valves, such as the aortic, mitral, pulmonary, and tricuspid valves. For example, a trocar or other suitable device may be used to penetrate the heart at or near the apex of the heart. A delivery member, such as a catheter, can then be movably disposed within the trocar. The delivery member may comprise a balloon expansion member and a stented prosthetic valve collapsed around the balloon expansion member. The delivery member may also comprise a number of other devices useful in conjunction with performing valve replacement surgery, such as a valve removal device, valve sizer, and/or an imaging system.

After the trocar penetrates the apex of the patient's heart, the delivery member may be introduced therethrough. The stented prosthetic valve may then be positioned for implantation at a desired location within or near the heart. Once in position, the balloon expansion member is inflated by the infusion of gas or fluid, preferably saline, to expand and deploy the stented prosthetic valve at the desired location.

Self-expanding prosthetic valves may also be used in connection with the apical approach to valve replacement surgery. In this embodiment, a balloon expansion member is not required since the valve stent is self-expanding. Instead, the self-expanding prosthetic valve is positioned around the delivery member and introduced through the apex of the heart and delivered to the site of implantation. Self-expanding stented prosthetic valves suitable for use in connection with apical valve replacement surgery are described more fully in co-pending U.S. patent application Ser. No. 10/680,717, filed Oct. 6, 2003, which is incorporated herein by reference.

Figure 1:
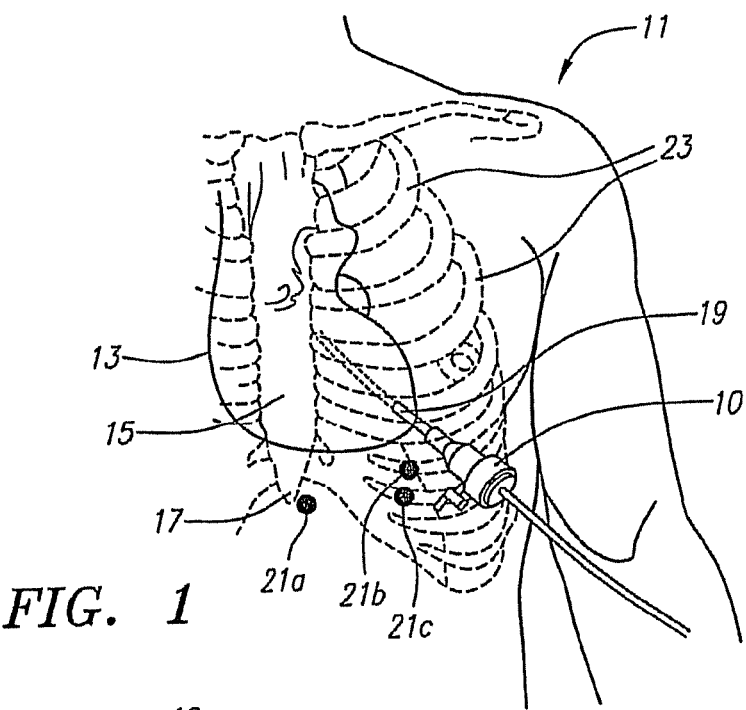
FIG. 1 is a partial front view of a patient's chest showing a replacement valve deliver device introduced through the apex of the heart through the fifth intercostal space.

FIG. 1 shows the position through which the distal embolic protection assembly may be delivered through patient's chest (11) and through the apex of the patient's heart (13) in relation to other anatomical landmarks, such as the sternum (15), xiphoid (17), ribs (23) and heart (13). The trocar (10) is depicted as entering the chest (11) through the fifth intercostal space (19) and through the apex of the heart (13). The trocar (10) may also enter the body cavity through various other locations (21A, 21B and 21C) in the patient's chest (11) in order to access the apex of the patient's heart (13). Entry through the apical area of the heart permits ease of access to the valves and the great vessels of the patient's heart.

Figure 2:
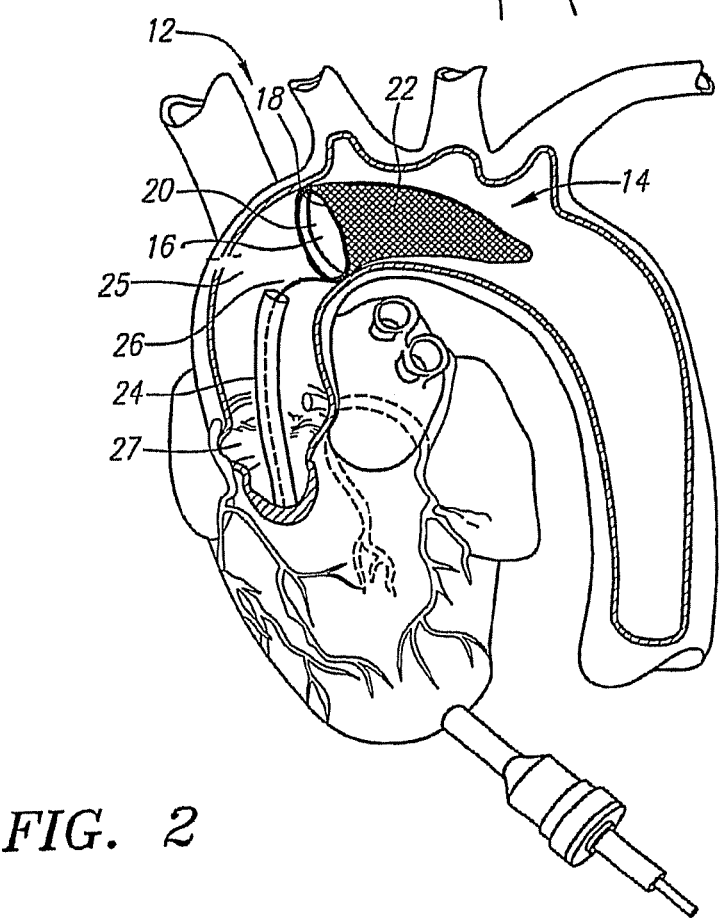
FIG. 2 shows the distal embolic protection assembly deployed in the aorta via apical area access.

A distal embolic protection assembly as disclosed herein may be implanted at a location downstream from the site where valve repair or replacement surgery is to be performed. One embodiment of the distal embolic protection assembly (12) is depicted in FIG. 2, which shows the filter assembly (14) positioned in the aorta (25) and downstream of the aortic valve (27). In this embodiment, the filter assembly (14) is comprised of a one-way valve (16) coupled to the frame (18) at the inlet proximal end (20) of the porous bag (22) extending therefrom.

The distal embolic protection assembly (12) provides distal embolic protection and may be delivered by a sleeve (24), such as a catheter or cannula, and deployed by manipulation of either the sleeve (24) or the actuation member (26) that is coupled to the frame (18) of the filter assembly (14). After the filter assembly (14) is deployed at its desired location, it serves the dual functions of a temporary check valve and a filter to capture any loose emboli or debris during surgery.

In one embodiment, the distal embolic protection assembly is introduced through the apex of the patient's heart, advanced through the left ventricle and across the aortic valve into the ascending aorta. Once the inlet end of the filter assembly is positioned in the ascending aorta between the aortic valve and the brachiocephalic artery, the frame of the filter assembly is either actively or passively deployed to its expanded state. As herein described, the filter assembly may be utilized for capturing embolic material that is dislodged as a result of procedures involving the repair or replacement of the aortic and mitral valves.

In another embodiment, the distal protection assembly may be introduced through the apex of the patient's heart, advanced through the right ventricle and placed downstream of the pulmonary valve and before the pulmonary trunk. At the pulmonary trunk, the pulmonary artery splits into the left and right pulmonary artery. Thus, in an alternative embodiment, two filter assemblies may each be placed in the left and right pulmonary artery. As herein described, the filter assembly may be utilized for capturing embolic material that is dislodged as a result of procedures involving the repair or replacement of the pulmonary and tricuspid valves.

The distal embolic protection assembly, as disclosed herein, may be used to place a filter assembly downstream of the valve before the commencement of valve repair or replacement surgery. Once in place, the filter assembly will allow for the capture and removal of embolic material and other debris from the patient after surgery has completed.

In one embodiment, the valve replacement system and the distal embolic protection system, as disclosed herein, may comprise a single and integrated piece of equipment. In accordance with this embodiment, a single catheter or sleeve may be used both for providing a valve replacement system and for providing the filter assembly downstream of the valve replacement system.

In another embodiment, the valve replacement system and the distal embolic protection system may comprise two separate pieces of equipment. As used in this manner, the catheter used to deliver the replacement valve is a structure that is separate from the distal embolic protection system. In one alternative embodiment, the filter assembly is first deployed at a location downstream from the valve that is to be replaced. The catheter comprising the replacement valve disposed thereon may then be provided on the sleeve or the actuating member of the distal embolic protection system. In this manner, a distinct advantage is conferred in that the sleeve or actuating member serves to guide the catheter comprising the replacement valve to the intended site of valve implantation.

A distinct advantage in using the apical approach over the percutaneous approach for valve replacement and repair surgery, particularly with respect to the valves of the heart, is that the surgeon has direct access to the valves and a larger working area. Any surgical device that must be delivered to the heart in connection with the percutaneous approach must be contracted to a very small profile to permit it to be delivered through the vasculature. The apical approach relaxes this size constraint considerably, as incisions of up to 25 mm may be made to the apical area of the heart.

The embodiment illustrated in FIGS. 3A and 3B show two perspective views of a distal embolic protection assembly (30) generally comprising a sleeve (32) having an lumen (34), an actuating member (36) having a proximal end (36A) and a distal end (36B), and a deployed filter assembly (42) in a blood vessel (31). The filter assembly (42) comprises a porous bag (44) having an open proximal end (46) and a collapsible and expandable frame (48) coupled to the open proximal end (46) of the porous bag (44). The filter assembly (42) may optionally comprise one or more support spines (50) disposed along at least a part of the longitudinal axis of the porous bag (44).

The sleeve (32) is configured and dimensioned to accommodate the actuating member (36) and to restrain the frame (48) of the filter assembly (42) within the lumen (34) in a sufficiently low profile to facilitate the advancement and retraction of the filter assembly (42) through the apex of the heart and to the site where the filter assembly (42) is to be implanted.

The sleeve (32) may be made of any rigid, semi-rigid and flexible biocompatible materials, such as metals, alloys, polymers, and the like, depending on its mode of use. For example, in cases where the filter assembly is implanted in an area of close proximity to the apical area of the patient's heart, such as when the filter assembly is implanted in the aorta, the sleeve may be made of a rigid or semi-rigid material. This is because the pathway between the apex and the aorta of the heart is a relatively short and straight distance. In cases where the filter assembly is implanted in a blood vessel at a greater and more convoluted distance from the apex, it may be desirable to use a sleeve that is made of flexible material so as to permit the delivery of the filter assembly through the convolutions in the passageway.

The lumen (34) of the sleeve (32) is sized to receive the actuating member (36) and the frame (48) in its collapsed state. The lumen (34) of the sleeve (32) may comprise a coating of Teflon, high density polyethylene or other similar material that promotes the smooth insertion and retraction of the frame (48) into and out of the lumen (34) of the sleeve (32). The dimension of the sleeve (32) and the lumen (34) may be configured to accommodate the entire filter assembly (42) or only the frame (48) of the filter assembly (42).

The actuating member (36) may be constructed from any biocompatible material, such as metal, alloys, polymers, and the like. Similarly as with the materials selected for the sleeve (32), the actuating member (36) may be constructed from rigid or semi-rigid material where the filter assembly is to be placed in relative close proximity to the apical area of the heart, such as the aorta. A rigid or semi-rigid actuating member (36) will permit greater control in the maneuvering and placement of the filter assembly (42) at its desired location. However, where the filter assembly (42) is to be implanted at a location that is farther away from the apical area of the heart, a flexible material may be used.

The collapsible and expandable frame (48) may formed from a shape memory material, such as Nitinol, that causes the frame (48) to expand to a predetermined shape and diameter when it unrestrained or released from the sleeve (32). The elasticity of the material causes the frame (48) to expand to a predetermined shape and size when outside of the sleeve (32) and to contract to a collapsed state when restrained within the lumen (34) of the sleeve (32).

In the embodiment shown in FIGS. 3A-B, the collapsible and expandable frame (48) has a pre-determined substantially circular shape. The diameter of the frame (48) may be selected such that it substantially conforms to or is slightly larger than the inner diameter of the aorta or other vessel or body cavity in which placement of the filter assembly is desired.

In one embodiment of the frame depicted in FIGS. 3A-B, the actuating member (36) and the substantially circular frame (48) may be formed from a single piece of shape memory metal, such as Nitinol. In this embodiment, the shape of the substantially circular frame (48) and a angled kink (52) at the distal end (36B) of the actuating member (36) and the frame (48) are pre-shaped such that upon deployment of the filter assembly (42) from the lumen (34) of the sleeve (32), it assumes the shape that is depicted in FIGS. 3A-B.

A cloth or other protective covering (47) may optionally be provided around the frame (48) to ensure that the open proximal end (46) of the filter assembly (42) forms a seal with the walls of the blood vessel and to prevent embolic material or debris from becoming trapped within or pass between the open proximal end (46) and the walls of the blood vessel (31). In addition, the cloth covering will protect the aortic wall from becoming damaged by the expanding frame (48) of the filter assembly (42).

The porous bag (44) of the filter assembly (42) may be a mesh of any size and shape required to trap all of the embolic material while still providing sufficient surface area for providing satisfactory blood flow during use. The filter may be a sheet or bag of different mesh sizes. In a preferred embodiment, the mesh size is optimized taking into consideration such factors as flow conditions, application site, size of filter bag, and rate of clotting.

For example, the porous bag (44) may be made of a fine mesh material, such as a screen, or may be a woven or knitted fabric, such as Dacron polyester or nylon mesh or other textile fabrics. The porous bag (44) may also be a nonwoven fabric, such as a spun bonded polyolefin or expanded polytetrafluoroethylene or other nonwoven materials, or it may be a fine wire mesh or combination of any of the aforementioned materials. Preferably, the porous bag (44) has a pore size that permits blood to perfuse freely through, while capturing embolic material and other debris.

The porous bag (44). may have uniform pore size throughout or varying pore sizes in different areas. In one embodiment, the pore size of the. porous bag (44) may be in the range of 1 to 200 micrometers for capturing embolic material. Larger pore sizes may be selected for application in which the filter assembly is used to capture large debris, such as excised valve leaflets in connection with valve removal surgery.

The porous bag (44) may further comprise one or more support spines (50) that longitudinally extend at least a part of the length of the porous bag (44). The support spine (50) may be constructed into any shape and from any material of sufficient rigidity to support the porous bag (44) in substantially a lengthwise fashion and prevent porous bag (44) from collapsing into itself or from inverting inside-out. In one embodiment, the support spine (50) may simply be a rod that is coupled along the longitudinal axis of the porous bag (44). Further, the support spine (50) may either extend only partially along the porous bag (44) or extend the entire length of the porous bag (44).

Figure 4A:
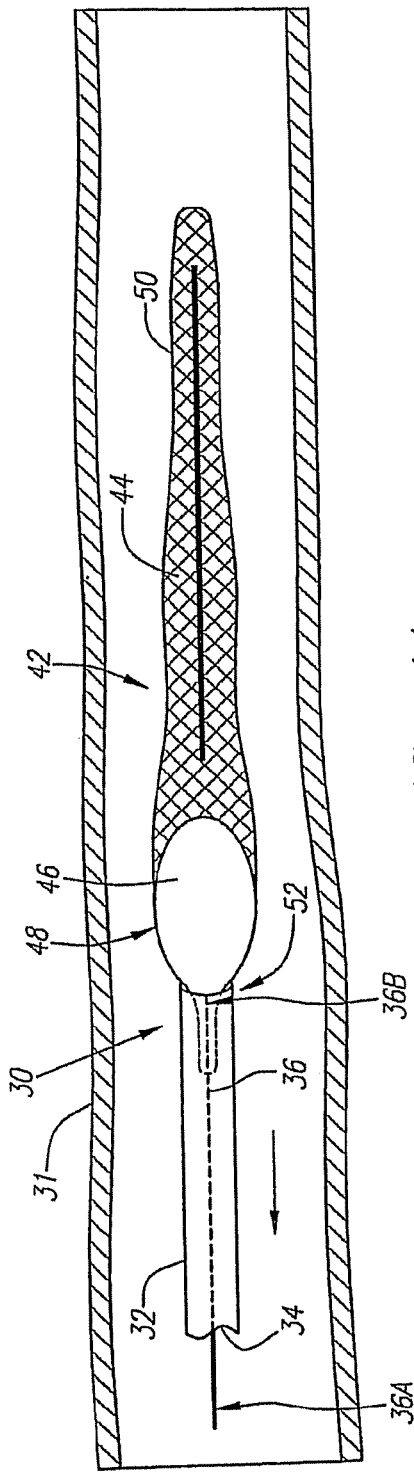
FIG. 4A shows the partial retraction and FIG. 4B shows the complete retraction of the frame of the filter assembly into the lumen.
Figure 4B:
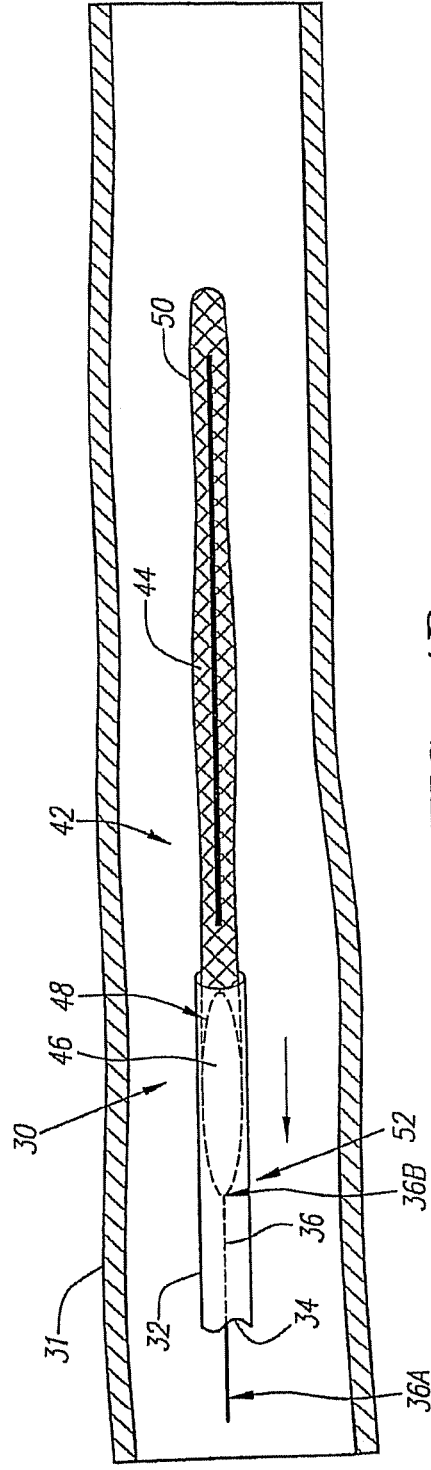

The filter assembly (42) is movable between an expanded deployed state (as shown in FIGS. 3A and 3B) and a collapsed state (as shown in FIGS. 4A and 4B) to permit the insertion and removal of the distal embolic protection assembly (30) in the patient. The frame (48) of the filter assembly (42) may be drawn into the lumen (34) of the sleeve (32) by manipulating the actuating member (36) in the proximal direction as indicated by the arrows in FIGS. 4A and 4B. This will retract and collapse the frame (48) and substantially close the open proximal end (46) of the porous bag (44). Alternatively, the sleeve (32) may be pushed in a distal direction toward the frame (48) of the filter assembly (42) to urge and collapse the frame (48) within the lumen (34). Retraction of the frame (48) of the filter assembly (42) may also be accomplished by the simultaneous and relative motion of the sleeve (32) and the actuation member (36) connecting the frame (48) towards one another and in opposite directions.

The retraction of the filter frame (48) into the lumen (34) of the sleeve (32) as shown in FIG. 4B will substantially reduce the likelihood of embolic material escaping out of the porous bag (44) as the filter assembly (42) is removed from the patient. The filter assembly may be removed from the patient once the frame is fully contained within the lumen of the sleeve. In this embodiment, because only the frame (48) of the filter assembly (42), and not the porous bag (44), is retracted within the lumen (34) of the sleeve (32), there a reduced likelihood that embolic material contained within the porous bag (44) will become squeezed out through the pores of the porous bag (44). Alternatively, the entire filter assembly, including the porous bag (44), may be fully retracted into the lumen of the sleeve. Full retraction of the filter assembly (42), including the porous bag (44), may not be possible where large emboli or debris, such as excised valve leaflets, are contained in the porous bag (44). Accordingly, where the large emboli and debris is contained, only the frame (48) should be retracted into the lumen (34).

In another embodiment, the frame (48) of the filter assembly (42) may take the form of a coil expansion frame that is made of a flexible polymer or shape memory material, such as Nitinol. The coil expansion frame may be configured such that when it is deployed to its expanded state, the diameter of the coil expansion frame conforms substantially to, or is slightly larger, than the diameter of the vessel in which it is placed.

The coil expansion frame further comprises a actuation member (36) which is integral to the coil expansion frame and disposed within the lumen (34) of the sleeve (32), wherein the actuation member (36) may be pulled in a proximal direction to decrease coil diameter of the coil expansion frame to cinch the open proximal end (46) of the porous bag (44) closed in a manner similar to a draw string bag. In this embodiment, the sleeve (32) does not receive the filter assembly (42) into the lumen (34) but functions as a means by which the actuation member (36) of the coil expansion frame may be pulled such that the coil expansion frame may be cinched closed for removal of the filter assembly (42) from the body.

FIGS. 5A and 5B show another embodiment of the distal protection assembly (60) comprising a sleeve (62) having an lumen (64), an actuating member (66) having a proximal end (66A) and a distal end (66B), and a filter assembly (72) in a blood vessel (59). The filter assembly (72) comprises a porous bag (74) having an open proximal end (76) and a collapsible and expandable stent frame (78) coupled to the open proximal end (76) of the porous bag (74). The filter assembly (72) may optionally comprise one or more support spines (80) disposed along at least a part of the longitudinal axis of the porous bag (74).

FIG. 5A shows the filter assembly (72) in its deployed and expanded state and FIG. 5B shows the stent frame of the filter assembly (72) in its collapsed state for placement and removal of the filter assembly (72) in the blood vessel (59). The stent frame (78) of the filter assembly (72) may be formed from a shape memory material, such as Nitinol, that causes the stent frame (78) to expand to a pre-determined shape and diameter when it unrestrained or released from the sleeve (62). The elasticity of the material causes the stent frame (78) to expand to a predetermined shape and size when outside of the sleeve (62) as shown in FIG. 5A and to contract to a collapsed state when restrained within the lumen (64) of the sleeve (62) as shown in FIG. 5B.

The stent frame (78) may be constructed in any number of configurations designed to substantially support the open proximal end (76) of the porous bag (74) open when it is in a deployed state. The deployed filter assembly (72) depicted in FIG. 5A shows a stent frame (78) comprising a proximal collapsed end (78A) that remains within the lumen of the sleeve and an expanded distal end (78B) that is coupled to and supports the open proximal end (76) of the porous bag (76). The longitudinal arms (77) of the stent frame (78) joins the proximal collapsed end (78A) and the expanded distal end (78B) and the longitudinal arms (77) are biased to expand radially to a deployed state. As the stent frame (78) is retracted into the lumen (64) of the sleeve (62), the longitudinal arms (77) are urged to radially compress the expanded distal end (78B) of the stent frame (78) to a collapsed state.

Figure 5C:
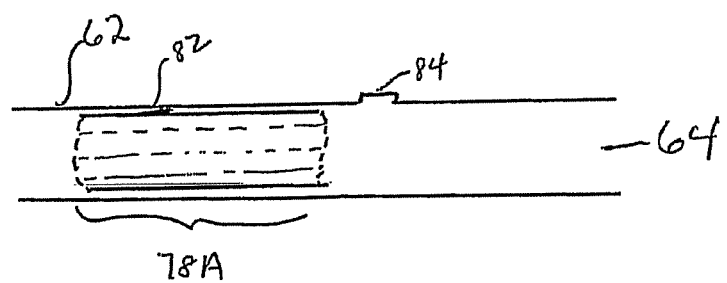
FIG. 5C depicts the stop latch of the present invention prior to engaging the matching groove.
Figure 5D:
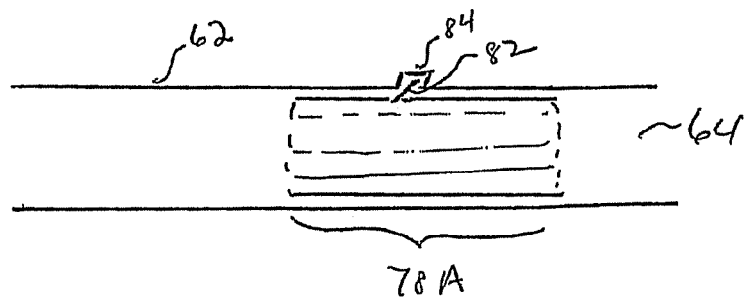
FIG. 5D depicts stop latch in engagement with the matching groove of the present invention.

The distal protection assembly (60) further comprises a means for preventing the proximal collapsed end (78A) of the stent frame (78) from exiting the lumen (64) of the sleeve (62) when the filter assembly (72) is deployed. While a number of different methods and mechanisms may be used to prevent the stent frame from fully exiting the lumen of the sleeve, the distal protection assembly depicted in FIG. 5A shows a stop latch (82) that is biased in a forward direction on the proximal collapsed end (78A) of the stent frame (78) which mates with a matching groove (84) contained within the lumen (64) of the sleeve (62). The mating of the stop latch (82) to the grove (84) prevents the proximal collapsed end (78A) from exiting the lumen (64) during deployment of the filter assembly (72)

from the sleeve (62). FIG. 5C shows detail of the stop latch (82) of the present invention prior to engaging the matching groove (84) in the lumen of sleeve (62). FIG. 5D shows further detail of stop latch 82 in engagement with the matching groove 84 to prevent the proximal collapsed end (78A) of the stent frame (78) from exiting the lumen (64) of the sleeve (62) when the filter assembly (72) is deployed.

In FIG. 5B, the frame of the filter assembly (72) is shown in its retracted state and contained in the lumen (64) of the sleeve (62). The retraction of the stent frame (78) is accomplished in the same manner as described above for FIGS. 4A and 4B. As the actuating member (66) is pulled in a proximal direction or as the sleeve (62) is pushed in a distal direction, the longitudinal arms (77) of the stent frame (78) is radially urged to a collapsed position to facilitate the retraction of the expanded distal end (78B) of the stent frame (78) into the lumen (64).

Figure 6A:
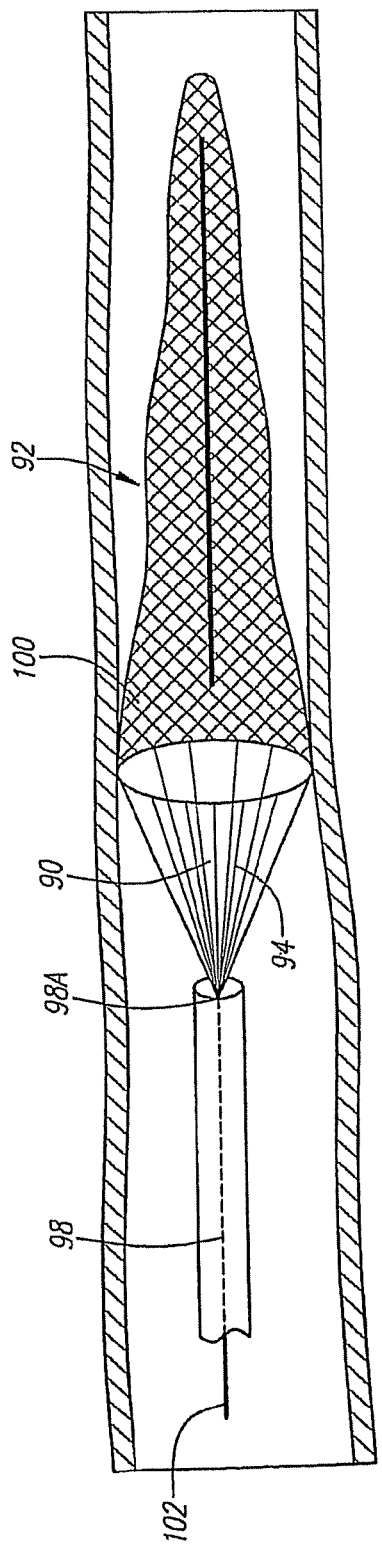
FIG. 6A shows the filter assembly in its deployed state and FIG. 6B shows the filter assembly in its collapsed state for insertion into or removal from the patient's body.
Figure 6B:
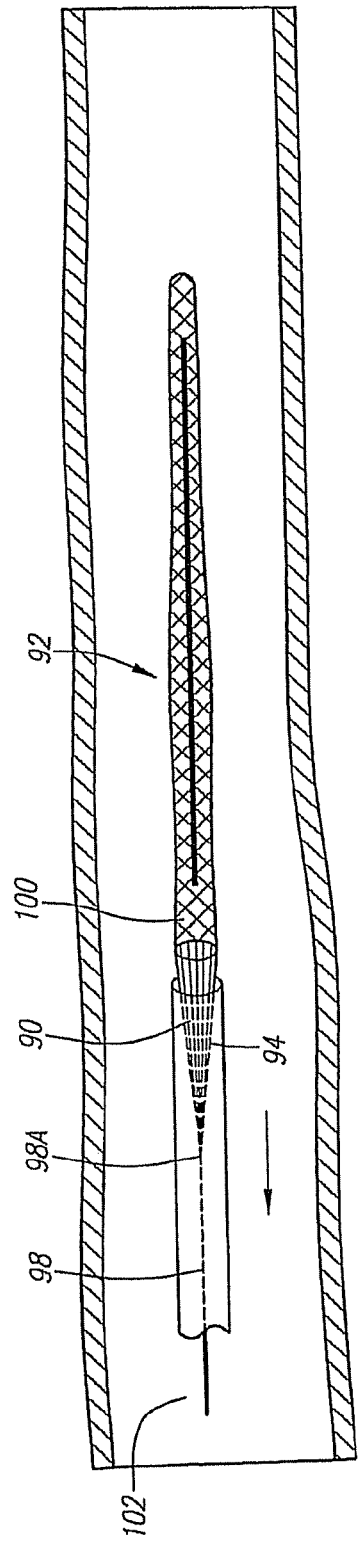

FIGS. 6A and 6B show yet another embodiment in which the frame (90) of the filter assembly (92) comprises a plurality of arms (94) which converge at the distal end (98A) of the actuating member (98) and extend radially outward and are coupled to the open proximal end (100) of the filter assembly (92). As shown in FIG. 6A, the arms (94) are adapted to expand radially upon deployment to substantially engage the open proximal end (100) of the filter assembly (92) with the walls of the blood vessel. The plurality of arms (94) function to actuate between the collapsed state of the filter assembly (92) when it is retracted in the sleeve (102) (as shown in FIG. 6B) and the expanded and deployed state of the filter assembly (92) when it is outside of the sleeve (102) (as shown in FIG. 6A).

Figure 7A:
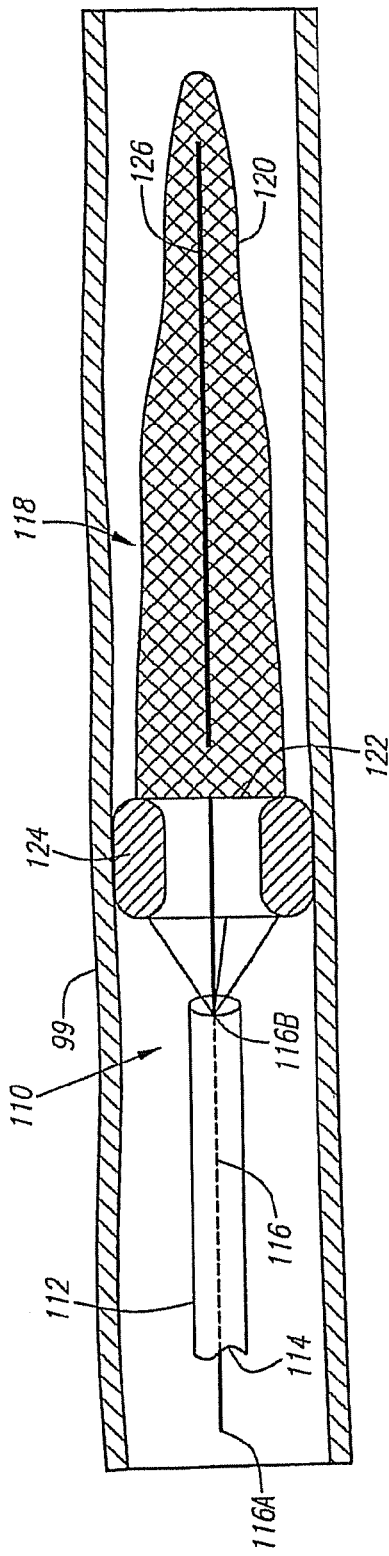
FIG. 7A shows the filter assembly in its deployed state and FIG. 7B shows the filter assembly in its collapsed state for insertion into or removal from the patient's body.
Figure 7B:
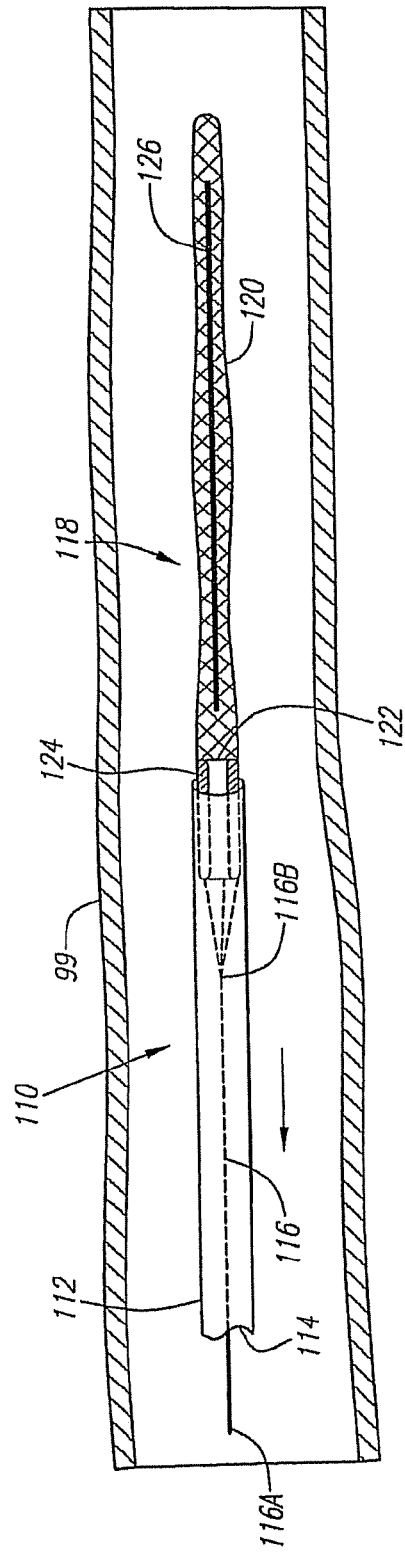

FIGS. 7A and 7B illustrate yet another embodiment of the distal embolic protection assembly (110) comprising a sleeve (112) having an lumen (114), an actuating member (116) having a proximal end (116A) and a distal end (116B), and a filter assembly (118) in a blood vessel (99). The filter assembly (118) comprises a porous bag (120) having an open proximal end (122) and an inflatable balloon frame (124) coupled to the open proximal end (122) of the porous bag (120). The filter assembly (118) may optionally comprise one or more support spines (126) disposed along at least a part of the longitudinal axis of the porous bag (120).

The inflatable balloon frame (124) is in fluid communication with a peripheral saline reservoir through a conduit and may be substantially donut-shaped in the expanded and deployed state, as shown in FIG. 7A. Because the balloon frame (124) may be collapsed by deflating the balloon frame (124), the filter assembly (118) may be introduced into and removed from the patient in the collapsed state either within the sleeve (112) as shown in FIG. 7B or even without the sleeve (122).

In any one of the embodiments described herein, the filter assembly may include a one-way valve at the open proximal end of the porous bag to provide the dual function of acting as a temporary valve during valve replacement surgery and preventing embolic material from escaping out from the porous bag. Adding the one-way valve prevents embolic material from escaping out of the porous bag, thus reducing the incidence of embolization and blockage. A valve would concurrently provide a temporary valve for use during valve surgery. Combining both a filter and a valve in the same arrangement also creates a more compact device allowing more space for conducting other procedures.

FIGS. 8A-B show one-way valves in connection with the distal protection assembly of FIG. 3. FIG. 8A illustrates one embodiment of the sleeve (214) having an inner lumen (216) and a filter assembly (200) shown in FIG. 3 comprising a porous bag (202) having an open proximal end (204) and a substantially circular frame (206) coupled to the open proximal end (204). A bileaflet one-way valve (208) is coupled to the open proximal end (204) of the porous bag (202) to permit the substantially unidirectional blood flow through the filter assembly (200).

In the embodiment depicted in FIGS. 8A-B, the proximal end (212A) of the actuating member (212) is manipulated in the distal direction to deploy the frame (206) to its deployed state and in the proximal direction to compress the frame (206) in its collapsed state. The distal end (212B) of the actuating member (212) is attached to the porous bag (202) at a location distal from the open proximal end (204) and functions as a support spine for the porous bag (202) and for the bileaflet valve (208). An additional support rod (210) is provided on the porous bag (202) to support the bileaflet valve (208) to the porous bag (202).

FIG. 8B shows an embodiment of the filter assembly (200) having a trileaflet valve (220) coupled to the open proximal end (204) of the porous bag. Because this valve has three leaflets, two support rods (210) are provided on the porous bag to support the trileaflet valve (220) to the porous bag (202). Although FIGS. 8A and 8B show the filter assembly in connection with bileaflet and trileaflet valves, respectively, a valve of any number of leaflets may be used so long as the valve permits substantially the unidirectional flow of blood and materials through the filter assembly and substantially reduces the back flow of blood and materials in the reverse direction.

Suitable valves may be constructed from a variety of flexible material such as from natural tissue, polymers or plastics. The valves may be constructed to the frame at the open proximal end of the porous bag with commissural tabs that attach the valves to the frame. The construction of valves suitable for use in connection with the filter assemblies herein are disclosed in U.S. Pat. No. 6,736,846, issued May 18, 2004; U.S. Pat. No. 6,719,789, issued Apr. 13, 2004; U.S. Pat. No. 6,719,788, issued Apr. 13, 2004; U.S. Pat. No. 6,682,559, issued Jan. 27, 2004; U.S. Pat. No. 5,344,442, issued Sep. 6, 1994; U.S. Pat. No. 5,500,015, issued Mar. 19, 1996 and in Ser. No. 10/173,188, filed Jun. 17, 2002; Ser. No. 10/668,650, filed Sep. 23, 2003; and Ser. No. 60/565,118, filed Apr. 23, 2004, which are herein incorporated in their entireties.

Although FIGS. 8A and B show the one-way valve in connection with the filter assembly of FIG. 3 having the substantially circular frame, the one-way valve may easily be adapted to a variety of frames in a number of ways. For example, the valve may be coupled to the stent frame of the filter assembly of FIG. 5 with relative ease, as the stent provides several points of attachment for the valve. The manner of including a one-way valve to stent frames is fully disclosed in co-pending U.S. patent application Ser. No. 10/680,717, filed Oct. 6, 2003, which is incorporated herein by reference.

Additionally, an imaging system to view the operating field may be used at any time or throughout the duration of the surgery. Imaging systems are well-known to one of skill in the art and include transesophageal echo, transthoracic echo, intravascular ultrasound imaging (IVUS), or an injectable dye that is radiopaque. Cinefluoroscopy may also be utilized. In one embodiment, the imaging system is deliverable through a catheter or cannula to the operating field.

Intravascular ultrasound (IVUS) uses high-frequency sound waves that are sent with a device called a transducer. The transducer may be coupled to the delivery member of the present invention. In this arrangement, the sound waves bounce off of the walls of the vessel or heart and return to the transducer as echoes. Methods and systems for IVUS imaging for the placement of heart valves is disclosed in co-pending U.S. patent application Ser. No. 60/529,242, filed Dec. 12, 2002, which is incorporated herein by reference.

Although the invention has been described with reference to preferred embodiments and specific examples, those of ordinary skill in the art will readily appreciate that many modifications and adaptations of the invention are possible without departure from the spirit and scope of the invention as claimed hereinafter.

What is claimed:

1. A method for providing distal embolic protection during cardiovascular surgery, the method comprising:
    creating an incision at or near the apex of a patient's heart;
    collapsibly introducing a distal embolic protection assembly into the apex of the heart, the distal embolic protection assembly comprising
    a sleeve having a sleeve lumen with a stop latch matching groove;
    an actuating member having proximal and distal ends, wherein the actuating member is movably disposed within the sleeve lumen; and
    a filter assembly coupled to the distal end of the actuating member, the filter assembly comprising a porous bag having an open proximal end, and a collapsible and expandable frame comprising a stent coupled to the open proximal end of the bag;
    wherein the actuating member is configured to be pulled in a proximal direction to compress and retract the frame within the lumen of the sleeve and retain the frame in a collapsed state and wherein the actuating member is configured to be pushed in a distal direction out of the lumen to a deployed expanded state; and
    wherein the stent comprises
    a proximal collapsed end that remains within the sleeve lumen;
    a stop latch protruding from and biased in a distal direction, the stop latch being adapted to mate with the stop latch matching groove when the stent is expanded to a deployed condition;
    an expanded distal end that is coupled to and supports the open proximal end of the porous bag; and
    longitudinal arms joining the proximal collapsed end and the expanded distal end, the longitudinal arms being biased to expand radially to a deployed state;
    advancing the sleeve through the apex of the heart and to a target location downstream of an area in which valve repair or replacement surgery is to be performed;
    positioning the sleeve at or near the target location; and
    deploying the filter assembly by removing the frame from the lumen at the target location.

2. The method of claim 1, wherein the incision is created by inserting a trocar having a diameter of approximately 12 mm through the apex of the heart.

3. The method of claim 2, wherein the sleeve is advanced through the apex of the heart via the trocar, through the left ventricle and across the aortic valve and into the ascending aorta.

4. The method of claim 3, wherein the target location for deployment of the distal embolic protection assembly is in the ascending aorta between the aortic valve and the brachiocephalic artery.

5. The method of claim 2, wherein the sleeve is advanced through the apex of the heart via the trocar, through the right ventricle and downstream of the pulmonary valve and before the pulmonary trunk.

6. The method of claim 5, wherein the target location for deployment is the area between the pulmonary valve and the pulmonary trunk.

7. The method of claim 1, wherein the porous bag comprises at least one support spine disposed along at least a part of a longitudinal axis of the porous bag.

8. The method of claim 7, wherein the porous bag comprises a plurality of support spines.

9. The method of claim 1, wherein the stent is made of a shape memory metal.

10. The method of claim 1, wherein the collapsible and expandable frame is configured to have a diameter that conforms to or is slightly larger than the diameter of a blood vessel.

11. The method claim 1, wherein the collapsible and expandable frame and the actuating member are formed from a single piece of shape memory metal.

12. The method of claim 11, wherein a kink is pre-shaped at the junction of the frame and the distal end of the actuating member so as to urge the frame at an angle from the axis of the actuating member.

13. The method of claim 11, wherein the frame further comprises a cloth covering the open proximal end of the filter assembly.

14. The method claim 1, wherein the distal embolic protection assembly further comprises a one-way valve and at least one support rod disposed on the porous bag to support the one-way valve along a longitudinal axis of the porous bag.

15. A method for providing distal embolic protection during cardiovascular surgery, the method comprising:
    creating an incision at or near the apex of a patient's heart;
    collapsibly introducing a distal embolic protection assembly into the apex of the heart, the distal embolic protection assembly comprising
    an actuating member having proximal and distal ends; and
    a filter assembly coupled to the distal end of the actuating member, the filter assembly comprising a porous bag having an open proximal end, a collapsible and expandable frame comprising an inflatable balloon member, the collapsible and expandable frame being coupled to the open proximal end of the bag, the inflatable balloon member being configured to be inflated from a collapsed state to a deployed expanded state;
    advancing the distal embolic protection assembly through the apex of the heart and to a target location downstream of an area in which valve repair or replacement surgery is to be performed; and
    deploying the filter assembly by inflating the inflatable balloon member at the target location.

16. The method of claim 15, wherein the inflatable balloon member is substantially donut-shaped in the inflated and deployed state.

17. The method of claim 15, wherein:
    the distal embolic protection assembly further comprises a sleeve having a sleeve lumen;
    the actuating member is movably disposed within the sleeve lumen; and
    deploying the filter assembly further comprises removing the frame from the lumen of the sleeve at the target location.

18. A method for providing distal embolic protection during cardiovascular surgery, the method comprising:
    creating an incision at or near the apex of a patient's heart;
    collapsibly introducing a distal embolic protection assembly into the apex of the heart, the distal embolic protection assembly comprising
    a sleeve having a sleeve lumen;
    an actuating member having proximal and distal ends, wherein the actuating member is movably disposed within the sleeve lumen; and a filter assembly coupled to the distal end of the actuating member, the filter assembly comprising a porous bag having an open proximal end, and a collapsible and expandable frame coupled to the open proximal end of the bag;

wherein the actuating member is configured to be pulled in a proximal direction to compress and retract the frame within the lumen of the sleeve and retain the frame in a collapsed state and wherein the actuating member is configured to be pushed in a distal direction out of the lumen to a deployed expanded state;

advancing the sleeve through the apex of the heart and to a target location downstream of an area in which valve repair or replacement surgery is to be performed;

positioning the sleeve at or near the target location; and deploying the filter assembly by removing the frame from the lumen at the target location.

19. The method of claim 18, wherein the expandable and collapsible frame comprises a stent.

20. The method of claim 18, wherein the expandable and collapsible frame is made of a shape memory metal.

21. The method of claim 18, wherein the collapsible and expandable frame is substantially circular and is configured to have a diameter that conforms to or is slightly larger than the diameter of a blood vessel.

22. The method of claim 18, wherein the expandable and collapsible frame comprises a plurality of arms, the plurality of arms converging and coupled to the distal end of the actuating member and extending radially outward and coupled to the open proximal end of the porous bag.

* * * * *